(12) United States Patent
Keshet et al.

(10) Patent No.: US 6,653,132 B1
(45) Date of Patent: Nov. 25, 2003

(54) IRES SEQUENCES WITH HIGH TRANSLATIONAL EFFICIENCY AND EXPRESSION VECTORS CONTAINING THE SEQUENCE

(75) Inventors: Eli Keshet, Jerusalem (IL); Ilan Stein, Jerusalem (IL); Ahuva Itin, Jerusalem (IL)

(73) Assignee: QBI Enterprises, Ltd., Nes Ziona (IL)

( * ) Notice: Subject to any disclaimer, the term of this patent is extended or adjusted under 35 U.S.C. 154(b) by 0 days.

(21) Appl. No.: 09/367,419

(22) PCT Filed: Feb. 25, 1998

(86) PCT No.: PCT/US98/03699

§ 371 (c)(1),
(2), (4) Date: Jan. 11, 2001

(87) PCT Pub. No.: WO98/37189

PCT Pub. Date: Aug. 27, 1998

Related U.S. Application Data

(60) Provisional application No. 60/038,500, filed on Feb. 25, 1997.

(51) Int. Cl.[7] ............................ C12N 5/02; C12N 15/11; C12N 15/63
(52) U.S. Cl. ..................... 435/375; 435/320.1; 536/24.1
(58) Field of Search ...................... 536/24.1; 435/320.1, 435/375

(56) References Cited

FOREIGN PATENT DOCUMENTS

| WO | 9514775 | 6/1995 |
|---|---|---|
| WO | 9821321 | 5/1998 |

OTHER PUBLICATIONS

Richard A. Morgan et al, Retroviral vectors containing putative internal ribosome entry sites: development of a polycistronic gene transfer system and applications to human gene therapy, Nucleic Acids research, vol. 20, No. 6, 1293–1299, Feb., 1992.*

Shu–Yun Le et al, A common RNA structural motif involved in the internal initiation of translation of cellular mRNAs, pp 362–369, Nucleic Acids research, 1997, vol. 25, No. 2.*
Cohen et al. Interlukin 6 induces the expression of vascular endothelial growth factor. J. Biol. Chem., 1996;271(2):736–741.
Shima et al. The mouse gene for vascular endothelial growth factor: Genomic structure, definition of the transcriptional and post–transcriptional regulatory sequences. J. Biol. Chem. 1996;271(7):3877–3883.
Vagner et al. Alternative translation of human fibroblast growth factor 2 mRNA occurs by internal entry of ribosomes. Mol. and Cell. Biol. 1995;15(1):35–44.
Vagner et al. Translation of CUG–but not AUG–initiated forms of human fibroblast growth factor 2 is activated in transformed and stressed cells. J. Cell Biol. 1996;135(5):1391–1402.
Bernstein et al. PDGF2/c–sis mRNA leader contains a differentiation–linked internal ribosomal entry site (D–IRES). J. Biol. Chem. Apr. 4, 1997;272(14):9356–9362.

* cited by examiner

*Primary Examiner*—Terry McKelvey
(74) *Attorney, Agent, or Firm*—John P. White; Cooper & Dunham LLP

(57) ABSTRACT

An isolated and cloned translation control element, and analogues thereof, having the nucleotide sequence as set forth in SEQ ID NO:7 and designated SP163, are disclosed. The translation control element controls cap-independent mRNA translation via an internal ribosome entry site (IRES). The present invention provides expression vectors comprising the translation control element SP163 or its analogues operatively linked to a gene sequence to be expressed. In alternative embodiments, the expression vector comprises at least two nucleic acid sequences to be translated and SP163 is operatively linked to at least one of the sequences to be translated. The sequences to be translated may be linked to only one promoter in an embodiment. The present invention further provides a method for facilitating and enhancing cap-independent translation of mRNA by including in an expression cassette a translation control element having the nucleotide sequence as set forth in SEQ ID NO:7 and designated SP163.

18 Claims, 8 Drawing Sheets

IRES SEQUENCES WITH HIGH TRANSLATIONAL EFFICIENCY AND EXPRESSION VECTORS CONTAINING THE SEQUENCE

This application is a §371 national stage of PCT/US98/03699 filed Feb. 25, 1998, which claims the benefit of U.S. Provisional Application No. 60/038,500, filed Feb. 25, 1997.

BACKGROUND OF THE INVENTION

1. Field of the Invention

The present invention relates to an isolated and cloned DNA sequence element that can be incorporated into expression vectors for the purpose of improving translation of a given mRNA and to enable the translation of the mRNA in a cap-independent manner.

2. Description of Related Art

There is an extensive and growing need to produce eukaryotic gene products in eukaryotic cells. Methods are needed to maximize expression of a desired gene and production of the gene product in eukaryotic cells. Initiation of eukaryotic protein synthesis involves about ten initiation factors, eIFs. The eIF4 group of initiation factors collectively catalyze the recognition of the mRNA cap, the unwinding of mRNA secondary structure, and the binding of mRNA to the 43S preinitiation complex [Pain, 1996]. The selection of a particular mRNA from the pool of translatable RNAs is determined by the relative efficiency of translation initiation by ribosome scanning and is largely governed by the composition and structure of the 5'-untranslated region (5'UTR) of the mRNA [Kozak, 1991; Sonenberg, 1996].

In certain instances translation of the transcribed, processed, and end-modified (i.e. capped and polyadenylated) mRNA is the limiting step in the production of the protein [Mathews et al., 1996; Meyuhas et al., 1996]. Translation is initiated by mRNA-protein interactions preceding the engagement of the small ribosomal subunit (40S) with the mRNA. Thus, limited availability of cap-binding proteins and competition with other cellular mRNAs for that proteins can be a rate-limiting factor in translation of the desired protein. This limitation can be even more pronounced under stress conditions (e.g. heat shock, hypoxia, nutrient deprivation) in which cap-dependent translation is markedly compromised. [Mathews et al., 1996; Meyuhas et al., 1996].

An alternative mode of translation is one in which ribosomes bind to the mRNA independent of the cap structure using an internal ribosome entry site (IRES), a specialized sequence within the 5' untranslated regions that directly promote ribosome binding, independent of a cap structure. IRES elements were first discovered in picornaviral mRNAs which ate naturally uncapped but nonetheless efficiently translated [Jang et al., 1988; Pelletier and Sonenberg, 1988; Oh and Sarnow, 1995]. Subsequently, it was found that some cellular RNAs which are normally capped can be translated either by the 5' end-dependent scanning mechanism or by an internal ribosome binding mechanism. Generally, IRES cannot be identified by sequence homology; known IRES have been identified and defined functionally [Mountford and Smith, 1995]. It appears that it is the conformation of the IRES sequence that enables the binding on the ribosome.

The list of cellular genes shown to contain sequences mediating internal initiation within their 5'UTR includes the immunoglubulin heavy chain binding protein (BiP) [Macjak and Sarnow, 1991], anntennapedia [OH et al., 1992], fibroblast growth factor (FGF) [Vagner et al., 1995], platelet-derived growth factor-B (PDGF-B) [Bernstein et al., 1997], insulin-like growth factor II (IGF-II) [Teerink et al., 1995], and the translation initiation factor eIF4G [Gan and Rhoads, 1996]. The potential utility of a cap-independent translation mode is best demonstrated in the case of viral RNAs in circumstances where cap-dependent translation is completely abrogated (through cleavage of an essential cap-binding protein by a virus-encoded protease) and the translation machinery is taken-over by IRES-containing viral RNA [Pelletier and Sonenberg, 1988]. The option of internal initiation is an advantage for competition with other mRNAs when certain components of the eIF4 complex become rate-limiting and this option provides a given mRNA the ability to be translated at times when cap-dependent translation is compromised. Such circumstances may develop under hypoxia where overall protein synthesis is significantly inhibited [Heacock and Sutherland, 1988; Kraggerud et al., 1995] or other stress conditions.

It would be useful to have a small sequence element, derived from a naturally-occurring cellular 5'UTR, that endows any desired gene with the ability to be more efficiently translated, in general, and to be translated in a cap-independent manner, in particular. That is, it would be useful to have additional IRES sequences with high translational efficiency, to use in expression vectors, to control mRNA translation and therefore protein synthesis as well as in gene therapy vectors.

SUMMARY OF THE INVENTION

According to the present invention, an isolated and cloned translation control element, and analogues thereof, having the nucleotide sequence as set forth in SEQ ID No:7 and designated SP163, is disclosed. The translation control element controls cap-independent mRNA translation via an internal ribosome entry site (IRES). The present invention provides expression vectors comprising the translation control element SP163 or its analogues operatively linked to a gene sequence to be expressed. In alternative embodiments, the expression vector comprises at least two nucleic acid sequences to be translated and SP163 is operatively linked to at least one of the sequences to be translated. The sequences to be translated may be linked to only one promoter in an embodiment.

The present invention provides a method for facilitating and enhancing cap-independent translation of mRNA by including in an expression cassette a translation control element having the nucleotide sequence as set forth in SEQ ID No:7 and designated SP163.

The novel sequence element (designated SP163) is composed of sequences derived from the 5'-UTR of VEGF (Vascular Endothelial Growth Factor gene), however, in a novel arrangement that was presumably generated through a previously unknown mode of alternative splicing. Functional analysis has shown that SP163 functions as a significant stimulator of translation and as a mediator of cap-independent translation. Imterestingly, the full-length 5'-UTR of VEGF has fair IRES activity indicating that these stronger activities were generated by a specific molecular event causing the juxtaposition of two specific 5'-UTR segments.

The advantages of SP163 is that it is a natural cellular IRES element with a superior performance as a translation stimulator and as a mediator of cap-independent translation relative to known cellular IRES elements. Another advantage of SP163 is that these functions are maintained under stress conditions.

DESCRIPTION OF THE DRAWINGS

Other advantages of the present invention will be readily appreciated as the same becomes better understood by reference to the following detailed description when considered in connection with the accompanying drawings wherein:

FIG. 1A is bicistronic expression vector in which expression of a bicistronic mRNA is driven by a CMV virus promoter. A firefly luciferase (LUC) is translated from the first cistron and a secreted alkaline phosphatase (SeAP) from the second cistron. Putative IRES elements are inserted into the intercistronic space (ICS). FIG. 1B is Monocistronic expression vector in which SeAP expression is driven by a CMV virus promoter. Sequence elements tested for a translation-modulating activity are inserted upstream of the SeAP coding region.

FIGS. 2A–2C are graphs showing the production of Luciferase and SeAP from a bicistronic mRNA in stably transfected C6 cells wherein FIG. 2A is a graph of production of SeAP from the downstream cistron. Pools of stably transfected C6 clones were grown to 70% confluence, medium was replaced with a fresh medium (t=0) and aliquots were withdrawn at the indicated time points and analyzed for SeAP activity. Activity is expressed as cumulative units of SeAP in 1 ml of medium and is standardized to total protein. For testing SeAP production under hypoxia, cells were shifted to 1% oxygen at t=0 and further analyzed as above. FIG. 2B is a bar graph showing ratio of SeAP/LUC production in the different transfectants. SeAP/LUC ratio was calculated from the respective activities determined at the endpoint of the experiment (t=24 hrs.). FIG. 2C is a bar graph showing that under hypoxia stress where translation of LUC gene from the upstream cistron was reduced the rate of SeAP production was unaffected indicating internal initiation. Plasmid designation is as shown in FIG. 1. N=Normoxia, H=Hypoxia.

DETAILED DESCRIPTION OF THE INVENTION

Figure 1A:
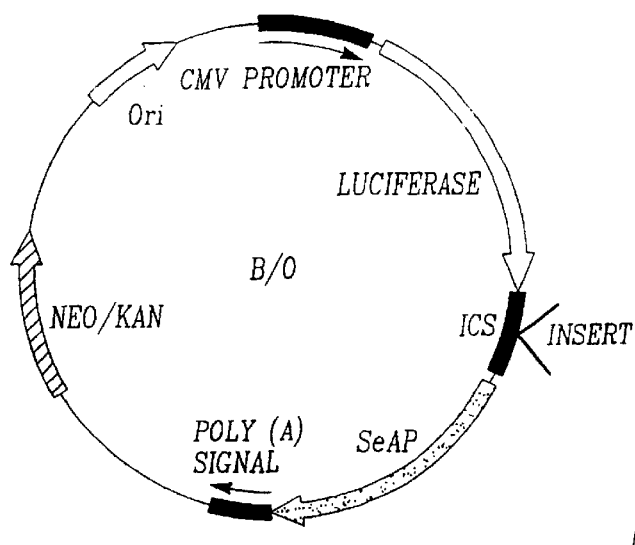
FIGS. 1A–1B are schematic diagrams of vectors and constructs used in this study.

According to the present invention, an isolated and cloned translation control element, and analogues thereof, having the nucleotide sequence as set forth in SEQ ID No:7 and designated SP163, is disclosed. The translation control element controls cap-independent mRNA translation via an internal ribosome entry site (IRES).

The term Analogue as used herein is defined as a nucleotide sequence variant (alternatively the terms alteration, sequence alteration, sequence variant can be used) with some differences in their nucleotide sequences as compared to the native sequence of SEQ ID No:7 but, such that the conformational folding of the sequence, to allow its use as an IRES, is not compromised. Ordinarily, the analogue will be generally at least 70% homologous over any portion that is functionally relevant. In more preferred embodiments the homology will be at least 80% and can approach 95% homology to the nucleotide sequence. The nucleotide sequence of an analogue may differ from that of the translation control element of the present invention when at least one nucleotide is deleted, inserted or substituted, but the translation sequence element remains functional as an IRES. Functionally relevant refers to the biological property of the sequence and in this context means a conformational or other aspects of the molecule that allow functioning as an enhanced IRES as described herein.

The present invention provides expression vectors comprising the translation control element, designated SP163, operatively linked to a gene sequence to be expressed. In alternative embodiments the expression vector comprises at least two nucleic acid sequences to be translated and the translation control element is operatively linked to at least one of the sequences to be translated. Vectors are known or can be constructed by those skilled in the art and contain all expression elements necessary to achieve the desired transcription of the sequences in addition to the sequence of the present invention as shown in the Examples herein below. The vectors contain elements for use in either procaryotic or eucaryotic host systems depending on their use. One of ordinary skill in the art will know which host systems are compatible with a particular vector.

Additional features can be added to the vector to ensure its safety and/or enhance its therapeutic efficacy as known in the art. Such features include, for example, markers that can be used to negatively select against cells infected with the recombinant virus. An example of such a negative selection marker is the TK gene that confers sensitivity to the antiviral drug gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type in addition to the translation control sequence of the present invention. As shown in the Examples herein the sequences can be used in all cell types in both vectors for use in cell culture and in vivo gene therapy.

The present invention also provides a method for facilitating preferential translation of a gene of interest over the bulk of cellular mRNAs which are not of interest. In other words allowing restriction of protein production in the host cell to essentially the protein/peptide coded for by the gene/nucleotide sequence of interest. The method provides the steps of including in an expression vector a translation control sequence of the present invention as set forth in SEQ ID No:7, operatively linked to the gene of interest. The vector is then expressed in host cells as is known in the art. The cells are then treated with compounds that inhibit cap-dependent translation. The reagents that are administered to the cell can include, for example, a virus-derived protease or anysomicin or other agents.

The present invention provides a second method for facilitating preferential translation of a gene of interest over the bulk of cellular mRNAs. In this further embodiment, the steps provide constructing an expression vector including a translation control sequence of the present invention as set forth in SEQ ID No:7, operatively linked to the gene of interest as well as any other required regulatory elements required for the sequence of interest. The vector is then expressed in host cells, as is known in the art. The host cells are then cultured under conditions which will induce cellular stress such as hypoxia, heat shock, hypoxia, hypoglycemia, iron deprivation and other conditions/treatments/compounds which will induce cellular stress such that cap-independent mRNA translation is active and cap-dependent translation is impaired.

As shown in the Examples, with the aid of reverse transcription-PCR, the use of mouse cytoplasmic mRNA as a template, and the primers indicated in Table 1 (corresponding to the 5' and 3' boundaries of the 5'-untranslated region of VEGF), the sequence of the present invention shown in Table 1, SEQ ID No:7, was amplified and subsequently cloned.

Comparison of this sequence (designated SP163; SEQ ID No:7) with known 5'-UTR VEGF sequences from rat [Levy et al, 1995], mouse [Shima et al, 1995] and human [Tischer et al, 1991] revealed that it is composed of the first 31 nucleotides of the 5'-UTR (including the cap) adjoined to the last 132 nucleotides of the 5'UTR (i.e. up to the initiator ATG condon). It appears that SP163 is generated by a splicing event that removes the bulk (>800 nucleotides) of internal 5'-UTR sequences.

Sequencewise, there is no obvious resemblance among the known cellular IRESs, nor do any of the cellular IRESs show a significant homology with picornavirus IRESs. For example, none of the known cellular IRESs has a pyrimidine-rich tract located 25 nucleotides upstream of the initiation site, as in the picornavirus IRESs [Ehrenfeld, 1996]. VEGF share a considerable sequence homology with another cellular gene that has an IRES element namely, PDGF. However, a search for sequence homology between the respective 5'UTRs have shown that, despite a similarity in length and overall high GC content, there is no significant homology in primary sequences.

Further Examples demonstrate that SP163 significantly improves production of a given protein, when included in various contexts of both moncistronic and bicistronic expression vectors. SP163, was introduced into the basic mono-cistronic expression vector pCIbb, and into the new bi-cistronic expression vectors pBIC-LS to create improved vectors (FIGS. 1A,B; Table 2). Experiments describing the performance of SP163 in the two vector systems are summarized as follows and detailed in the Examples.

In the mono-cistronic vector type (pBKC; M/O), FIG. 1B, SP 163 is introduced between the strong CMV promoter and the target gene. In this configuration, it enhances the expression of the gene located downstream. The secreted alkaline phosphatase reporter (SeAP) system is used to measure SP163 activity for testing its performance in different cellular conditions. This reporter system is especially convenient since it monitors the reporter activity in the growth media of the cells and allows the performance of elaborate kinetics studies.

Figure 1B:
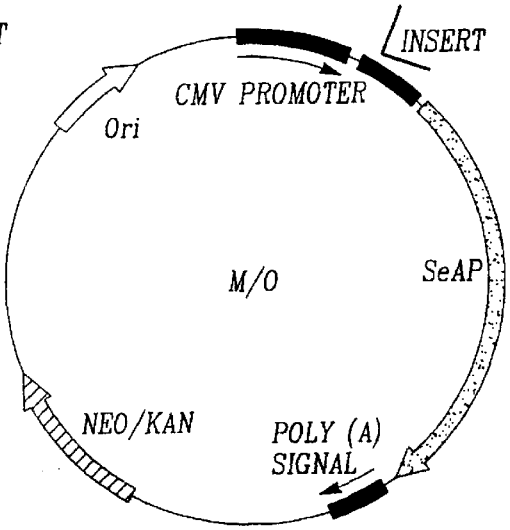

In the bi-cistronic vector system, FIG. 1A, SP163 is introduced between the two target recombinant genes. The expression of the first gene is driven by the strong CMV promoter, while that of the second is governed by cap-independent translation via the IRES element SP163. In the reporter version, bi-cistronic vector pBIC/LS (B/O; FIG. 1A), SP163 or any other IRES fragments studied are cloned into the unique multiple-cloning site element downstream to the luciferase (Luc) gene. The IRES element directs the expression of Secreted Alkaline Phosphatase (SeAP) via a cap-independent mechanism. The activity of the luciferase gene is used to normalize changes in transcription between different vectors containing different IRESs.

This embodiment of pBIC with the IRES of the present invention will allow the cloning of any two target genes, such as recombinant genes I and II, so that gene I will be expressed via the CMV promoter and gene II will be expressed via SP163.

Transient transfection is commonly used for characterization of the function of a cloned gene. In order to analyze the ability of SP163 to stimulate expression in transient transfection, the vectors pBKCS and pBKC163S were introduced into different cell lines by liposomes mediated transfection. As shown in the Examples, the results obtained indicate that in all the species tested the addition of SP163 to the pBKC/S vector leads to a significant stimulation of expression of 5–10 fold as measured by the reporter SeAP.

In the case of VEGF, internal ribosome entry circumvents the need for a troublesome ribosome scanning through the exceptionally long, highly structured 5'UTR which could have rendered translation an inefficient process [Kozak, 1991]. Among its many functions, VEGF plays an important role in maintaining vascular homeostasis and controlling vascular permeability [Senger et al., 1993]. Notably, its unscheduled downregulation at critical developmental timings may cause pathologic regression of existing vessels [Alon et al., 1995]. Thus, the capacity for cap-independent translation may serve as a safeguard, preventing the deleterious consequence of VEGF under-translation in circumstances where cap-dependent translation is transiently compromised.

The above discussion provides a factual basis for the use of IRES sequences with high translational efficiency and expression vectors containing the sequence. The methods used with and the utility of the present invention can be shown by the following non-limiting examples and accompaning figures.

EXAMPLES

General Methods

General methods in molecular biology: Standard molecular biology techniques known in the art and not specifically described are generally followed as in Sambrook et al., *Molecular Cloning: A Laboratory Manual,* Cold Springs Harbor Laboratory, New York (1989, 1992), and in Ausubel et al., *Current Protocols in Molecular Biology,* John Wiley and Sons, Baltimore, Md. (1989). Polymerase chain reaction (PCR) is carried out generally as in *PCR Protocols: A Guide To Methods And Applications,* Academic Press, San Diego, Calif. (1990). Reactions and manipulations involving other nucleic acid techniques, unless stated otherwise, are performed as generally described in Sambrook et al., 1989, *Molecular Cloning: A Laboratory Manual,* Cold Spring Harbor Laboratory Press, and methodology as set forth in U.S. Pat. Nos. 4,666,828; 4,683,202; 4,801,531; 5,192,659 and 5,272,057 and incorporated herein by reference. In-situ (In-cell) PCR in combination with Flow Cytometry can be used for detection of cells containing specific DNA and mRNA sequences [Testoni et al, 1996, Blood 87:3822]. The vectors of the present invention are synthesized as described herein and by any method known in the art.

Construction of bicistronic and monocistronic expression plasmids. The basic bicistronic vector (designated B/0) and basic monocistronic vector (designated M/0) used in this study for insertion of 5'UTR elements were provided by QBI Enterprises Inc. (Rehovot, Israel). Their structures are described in FIGS. 1A&B.

5'UTR elements were obtained by RT-PCR amplification using the specific primers indicated below. Primers were designed in a way that each amplified fragment was bounded by XhoI (5') and NcoI (3') sites and was inserted between the XhoI (5') and BsmBI (3') sites of the intercistronic spacer of the bicistronic vector B/0 or into the same sites of the monocistronic vector M/0. In either case, the hybrid NcoI/BsmBI site recreated the initiator ATG codon of the SeAP cistron.

Cloning VEGF and BiP 5'UTRs: RNAs from hypoxic NIH3T3 cells or 293 cells, respectively, were reverse transcribed using 10 μg of total RNA. PCR amplification was carried out using a Taq DNA Polymerase possessing a proofreading activity (Pwo DNA Polymerase, BOEHRINGER) and the following oligonucleotide primers: VEGF 5' primer: 5' CTCGAGCGCAGAGGCTTGGGGC (SEQ ID No:1). VEGF 3' primer: 5'CCATGGTTTCGGAG- GCCGTCCG 3' (SEQ ID No:2) corresponding to nucleotides 1218–1235 and 2234–2214, respectively, of the mouse VEGF gene (GeneBank accession U41383). The oligonucleotide primers used to amplify the full length VEGF 5'UTR were also used to amplify the new splice variant of VEGF 5'UTR designated SP163 which was also inserted into the B/0 and M/0 vectors in the same way as described above. BiP 5' primer: 5'CTCGAGAGGTC-GACGCCGGCCAAGACA (SEQ ID No:3). BiP 3' primer: 5'CCATGGCTTGCCAGCCAGTTGGGCAGC (SEQ ID No:4) (corresponding to nucleotides 372–392 and 592–572, respectively, of the human BiP gene, Genebank accession M19645).

All plasmid constructs were sequenced to verify their structure and the preservation of open reading frames within PCR amplified fragments. A summary of bicistronic and monocistronic constructs used in this study is shown in Table 2 and FIGS. 1A–B.

Cell culture and DNA transfections: C6 cells, a clonal glial cell line derived from a rat glial tumor [Benda et al., 1968], were grown in Dulbeco-Modified Eagle's medium (DMEM) containing 5% fetal calf serum and antibiotics. The human cell line 293 (adenovirus-transformed fetal kidney cells), mouse NIH/3T3 cells and rat primary astrocytes were maintained in Dulbeco-Modified Eagle's medium (DMEM) containing 10% fetal calf serum and antibiotics. Primary rat astrocytes were prepared as described previously [Frangakis and Kimelberg, 1984].

Where indicated, cells were exposed to hypoxia (1% oxygen) using a $CO_2/O_2$ incubator (Forma Scientific) in which oxygen levels are monitored and adjusted automatically.

Transfections were performed using Lipofectin (GIBCO BRL) as follows: Cells were plated at a density of $1–2\times10^5$ Cells per 60-mm plate and grown for 24 hours, medium was replaced with a serum-free DMEM and 200 μl of DNA-Lipfctin suspension (containing 2 μg supercoiled plasmid and 15 μg of Lipofectin, preincubated at room temperature for 40 minutes) were added in a dropwise manner. Fourteen hours later, medium was replaced with a medium supplemented with serum and antibiotics and cells were incubated for additional 48 hours before splitting into a selection medium containing G418 (2mg/ml). Selection continued for 10–14 days and >50 individual G418-resistant clones were pooled for each plasmid.

For transient transfections, cells were seeded at a density of $2\times10^5$ cells per 1 mm well and transfected 24 hours later with 1 μg of DNA per well using the calcium phosphate procedure [Jordan et al., 1996]. Cells and media were harvested 36 hours post-transfection. Cell extracts were analyzed for luciferase activity or used for mRNA preparation (in the latter case, 10 μg of DNA was used to transfect $2–2.5\times10^6$ cells per 100 mm plate), while the media was used for analysis of SeAP activity.

RNA analysis: Total RNA was prepared by the guanidinium thiocyanate/phenol-chloroform extraction procedure [Chirgwin et al., 1979]. mRNA was purified from total cellular RNA using the mRNA Separator Kit (CLONTECH).

Analysis of mRNA in polysomal fractions: Protein synthesis was instantaneously arrested by treating the culture with cycloheximide (90 μg/ml) for 10 minutes. Cells were collected, washed with phosphate-buffered saline and kept at −70° C. until analyzed. Cell lysis, size fractionation of polysomes by sedimentation through sucrose gradients, and preparation of ribosome-associated RNAs were performed as described previously [Meyuhas et al., 1987].

Northern blotting: RNA was denatured in glyoxal and electrophoresed through a 1.0% agarose gel. RNAs were transferred onto a nylon-based membrane (GeneScreen plus, NEN) by the capillary blot procedure, and were hybridized with the indicated cDNAs, labeled with $^{32}$P by randomly primed DNA synthesis. For standardization, blots were rehybridized with a β-actin probe or, alternatively, ribosomal RNAs were visualized by staining with methylene blue prior to hybridization. For relative quantification, autoradiograms were scanned using a PhosporImager (FUJIX BAS 1000 Bio-Imaging Analyzer). Hybridization probes used were: VEGF (a 0.6 kB long mouse cDNA fragment encoding VEGF165) [Shweiki et al., 1992], β-actin [Minty et al., 1981], luciferase (a 1.7 kB long cDNA fragment including all of the coding region of firefly luciferase), and SeAP (a 1.5 kB long cDNA fragment including the coding region of the human SeAP).

RT-PCR: semi-quantitative RT-PCR was performed using a single tube, one step RT-PCR system (Access RT-PCR system, PROMEGA) and 20 cycles of amplification. Oligonucleotide primers used for reverse transcription and amplification of the various splicing variants of VEGF mRNA were:

5'GAGAGAATGAGCTTCCTACAG 3' (SEQ ID No:5) and
  5' TCACCGCCTTGGCTTGTCACA 3' (SEQ ID No:6)
  (derived from the common fifth and eighth exons, respectively). PCR products were resolved by agarose gel electrophoresis, and detected by blot-hybridization using a VEGF-specific, $^{32}$P-labeled cDNA probe.

Luciferase and SeAP analysis: Luciferase enzymatic activity in the cell extracts was determined using a commercial Luciferase Assay System (PROMEGA) and the procedure recommended by the supplier. Light generated was measured using Lumac/3M BIOCOUNTER M2010-luminometer.

SeAP activity released into the growth medium was determined as follows: medium was heated for 5 minutes at 65° C. and clarified by centrifugation. Aliquots were diluted in a SeAP buffer (1M Diethanolamine pH 9.8, 0.5 mM $MgCl_2$, 10m M L-homoarginine) in a 96 well plate and the enzymatic reaction (at 37° C.) initiated with the addition of 20 μl of 120 mM p-nitrophenylphosphate. The reaction product was determined using an ELISA reader at A450–630. The amounts of conditioned medium added and incubation times used were adjusted so that readings were within the linear range of the calibration curve obtained with a purified SeAP standard. Total protein was determined by the Bradford method [Bradford, 1976].

Example 1

Analysis of the Full 5'UTR of VEGF

The 5'UTR of vascular endothelial growth factor (VEGF) has several features which are incompatible with efficient ribosomal scanning. First, it is considerably longer (1014 nucleotides in the mouse) than most eukaryotic 5'UTRs. Second, it has a high G/C content (comprising 64% of 5'-UTR sequences and 80% of the 100 nucleotides preceding the translation initiation condon) and can potentially form complex stable secondary structures. Third, the 5'UTR contains a short open reading frame bounded by in-frame initiation and termination condons. The inherent difficulty for efficient ribosome scanning, on the one hand, and the possibility of IRES, on the other hand, prompted Applicants to examine if the VEGF mRNA is translated in a cap-independent mode.

In review, VEGF plays a key role in the initiation of blood vessel formation. VEGF is produced by and secreted from the tissue towards which new blood vessels eventually extend. A large body of evidence supports the premise that the amount of VEGF produced determines the magnitude of the angiogenic response through interaction with cognate receptors expressed on nearby endothelial cells. VEGF expression is tightly regulated in vivo and a deviation from the normal levels of VEGF might be detrimental to the vasculature. For example, a reduction of VEGF gene dosage by one half (in mice heterozygous for an inactivating mutation in VEGF) leads to severe vascular defects and early embryonic lethality [Carmeliet et al., 1996; Ferrara et al., 1996]. Conversely, over-expression of VEGF may lead to pathologies like retinopathy resulting from excessive proliferation of blood vessels [Aiello et al., 1994; Pe'er et al., 1995].

VEGF expression can be modulated in vitro by a variety of agents, including a number of cytokines, growth factors and steroid hormones. Yet, from a physiological point of view, regulation of VEGF by hypoxia is the most significant. Inefficient vascular supply and the resultant reduction in tissue oxygen tension, often lead to compensatory neovascularization acting to satisfy the metabolic needs of the tissue. Hypoxia-induced VEGF was found to be the key mediator of this feedback response [Plate et al., 1992; Shweiki et al., 1992]. VEGF is regulated by hypoxia at both the transcriptional and post-transcriptional levels.

Transcriptional regulation of VEGF is mediated by the transcription factor, hypoxia-inducible factor 1 (HIF-1) which accumulates under conditions of hypoxia and activates VEGF transcription through binding to specific promoter sequences [Forsythe et al., 1996]. Hypoxia also leads to stabilization of VEGF mRNA [Ikeda et al., 1995; Shima et al., 1995; Stein et al., 1995]. The intrinsically short half-life of VEGF mRNA (approximately 30 minutes) is significantly extended under stress, presumably through hypoxia-augmented binding of yet unidentified protein(s) to its 3'untranslated region [Levy et al., 1996]. Both mechanisms act to increase steady-state levels of VEGF mRNA. However, it is not known whether production of VEGF is also regulated at the level mRNA translation and, in particular, whether the mode or extend of VEGF translation is effected by hypoxia. VEGF is expected to be maximally produced under hypoxia in order to fulfill its function as a mediator of hypoxia-driven angiogenesis. These considerations led to the examination of the performance of the 5'UTR under conditions of hypoxic stress.

To determine the efficiency by which VEGF mRNA is translated, primary astrocyte cultures were grown, cytoplasmic extracts prepared and fractionated by centrifugation through a sucrose gradient into subpolysomal and polysomal fractions. The relative abundance of VEGF mRNA in these fractions was determined by quantitative RT-PCR. The bulk of VEGF mRNA was associated with polyribosomes, indicating that the majority of VEGF mRNA is engaged in active protein synthesis. These results suggested that VEGF mRNA is efficiently translated under normal growth conditions despite its cumbersome 5'UTR.

To determine whether translation of VEGF mRNA is inhibited under conditions of severe hypoxia, a similar analysis was carried out using cultures grown for 16 hours under 1% oxygen. Astrocytes were chosen for this study since they are the first cells to respond to hypoxia of neuronal tissues by upregulating VEGF mRNA expression and are, therefore, the cells responsible for the feedback angiogenic response [Stone et al., 1995]. The fraction of RNA associated with polyribosomes was reduced by 50% in comparison with cells grown under normoxia. This result is consistent with previous observations that hypoxia causes about 30–50% inhibition in overall protein synthesis [Heacock and Sutherland, 1988; Kraggerud et al., 1995]. Despite the general impairment of protein synthesis, the majority of VEGF RNA remained associated with polysomes. Notably, all isoforms of VEGF mRNA remained associated with the polyribosomal fraction, including the shortest VEGF121 which can accommodate no more than 3–4 ribosomes when translated at a theoretical maximal rate. In contrast to VEGF, the fraction of mRNA encoding ribosomal protein L19 that was associated with polyribosomes was reduced 2-fold under hypoxia in comparison to normoxia. These results suggest that translation of VEGF mRNA is not a rate-limiting step in production of this vital protein. Importantly, translation does not appear to be rate-limiting even under hypoxia where the steady-state level of VEGF mRNA is elevated by one order of magnitude [Shweiki et al., 1992].

The fact that translation of VEGF mRNA is very efficient despite its 'inappropriate' 5'UTR, prompted examination of whether VEFG mRNA can be translated by internal ribosome entry. Bicistronic mRNAs have been effectively used in vivo to demonstrate the existence of IRES in both picornaviral [Pelletier and Sonenberg, 1988] and cellular [Gan and Rhoads, 1996; Macejak and Sarnow, 1991] mRNAs as discussed herein above. A eukaryotic expression vector was constructed in which a CMV virus promoter drives expression of a bicistronic RNA. The first cistron in the bicistronic mRNA used in this study, encoded firefly luciferase (LUC) and should be translated by a conventional cap-dependent scanning mechanism. As ribosomes fail to continue scanning through the intercistronic region, the second cistron, encoding a secreted alkaline phosphatase (SeAP), should be translated only if preceded by an IRES. SeAP was chosen as the downstream cistron since secretion of the enzyme into the culture medium allows accurate quantification and continuous monitoring of protein synthesis.

To prevent leaky translation into the second cistron, the intercistronic region included termination condons in all possible reading frames. The 5'UTR of VEGF was subcloned by precise PCR amplification, inserted into the intercistronic spacer (ICS) region and transfected into a C6 rat glioma cell line. Pools of stably-transfected clones were prepared, each composed of >50 individual clones. Analysis of pools assured that possible differences in gene expression due to different integration sites are averaged. Reporter gene activity was determined in transfectants obtained with the bicistronic vector alone (designated B/0) and with the bicistronic vector containing the VEGF 5'UTR (designated B/UTR). The two constructs expressed a bicistronic mRNA from which LUC was translated with a comparable efficiency. Analysis of the downstream cistron, however, revealed that B/0 produced a negligible amount SeAP activity, confirming a minimal, if any, readthrough of ribosomes from the LUC to the SeAP cistron. In contrast, B/UTR directed the production of high levels of SeAP in a continuous manner (FIG. 3A), indicating that the 5'-untranslated region of VEGF contains a functional IRES element.

Figure 3A:
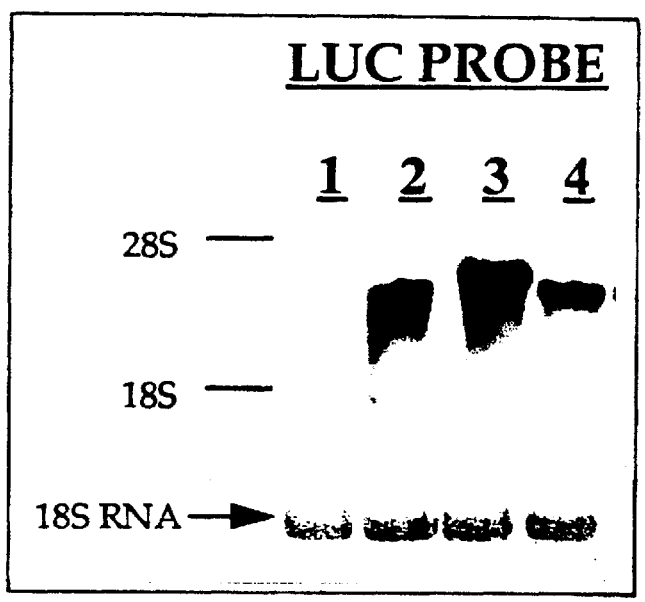
FIGS. 3A–3B are photographs of Northern blot analysis of mRNAs transcribed from bicistronic plasmids. RNA was extracted from untransfected C6 cells and from the same stably transfected C6 pools used in the experiment shown in FIG. 2. 20 µg of each RNA was electrophoresed in two parallel lanes, blotted and hybridized with either a LUC-specific probe (A) or a SeAP-specific probe (B). To assure equal loading, ribosomal RNAs were stained with methylene blue prior to hybridization. Lane 1—untransfected C6 cells; Lane 2—B/0; Lane 3—B/UTR; Lane 4—B/Bip.
Figure 3B:
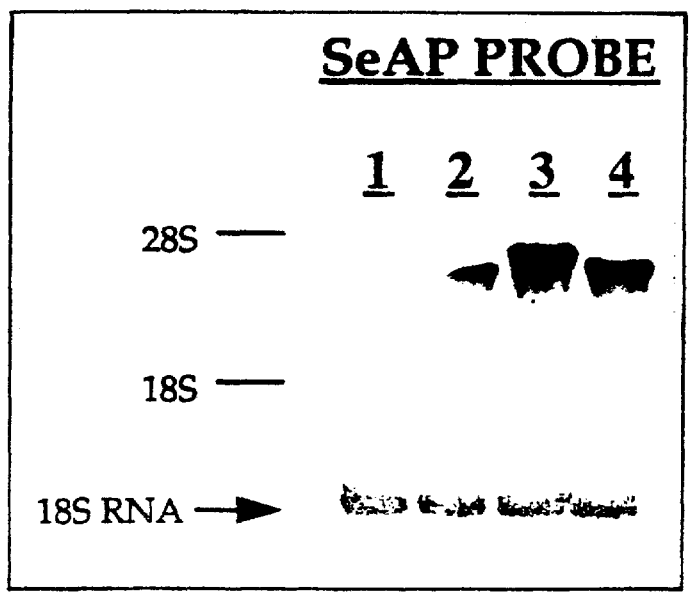

To appreciate the relative strength of the VEGF IRES, a comparison was made with the well-characterized cellular IRES contained in the 5'UTR of BiP mRNA [Pelletier and Sonenberg, 1988]. To this end, the 5'UTR of BiP was inserted into the same site of the bicistronic vector, pools of stable transfectants were prepared and similarly analyzed for LUC and SeAP production. As shown in FIG. 3B, the VEGF IRES was 5-fold more efficient than the BiP IRES in directing SeAP production.

Figure 2A:
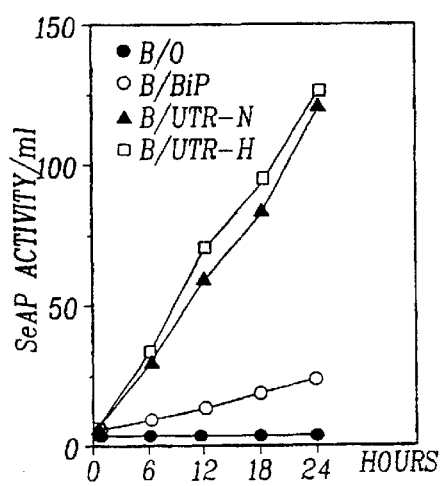
Figure 2B:
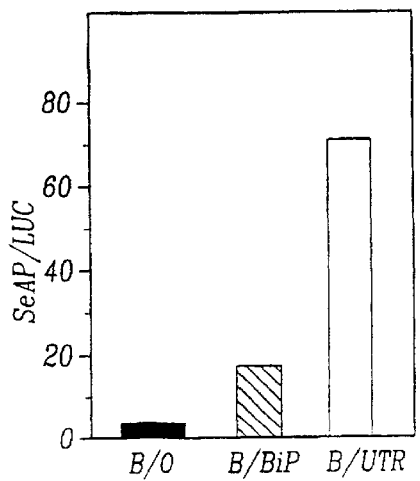
Figure 2C:
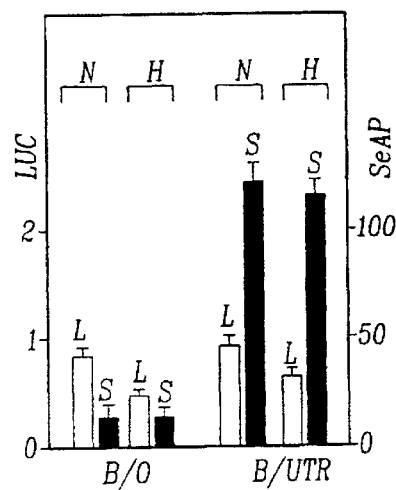

While there is a clear rationale for the use of internal initiation in viruses, the advantage of internal initiation in cellular mRNAs is not always clear. In the case of VEGF, however, the capacity for cap-independent translation might be particularly advantageous in hypoxia where overall protein synthesis is compromised. Therefore, we have measured SeAP production, presumably by internal initiation, was unaffected by hypoxia. As shown in FIGS. 2A and 2C, the rate of SeAP production, presumably by internal initiation, was unaffected by hypoxia.

To rule out that in B/UTR-transfected cells the protein encoded by the second cistron is translated from a monocistronic SeAP mRNA, a RNA blot-hybridization analysis was carried out using both a LUC-specific probe and a SeAP-specific probe. A single band of RNA was detected in each case, corresponding to the expected size of the respective bicistronic transcript (the larger size of hybridized mRNA in B/UTR-transfectants is due to the addition of 1014 base pairs of 5'UTR sequence) (FIGS. 3A,B). Hybridization with both a LUC-specific probe and a SeAP-specific probes detected the same mRNA species, indicating that both cistrons are contained in a single transcripts. Importantly, the failure to detect a band corresponding in size to that of a presumptive monocistronic seAP mRNA ruled out the possibility that a significant amount of SeAP is translated from a monocistronic SeAP mRNA. Also note that the inclusion of the 5'UTR had no effect on the steady-state level of the bicistronic mRNA expressed, indicating that differences in measured LUC and SeAP activities are solely due to differences in translation efficiencies.

Example 2

Identification of SP163

Figure 4:
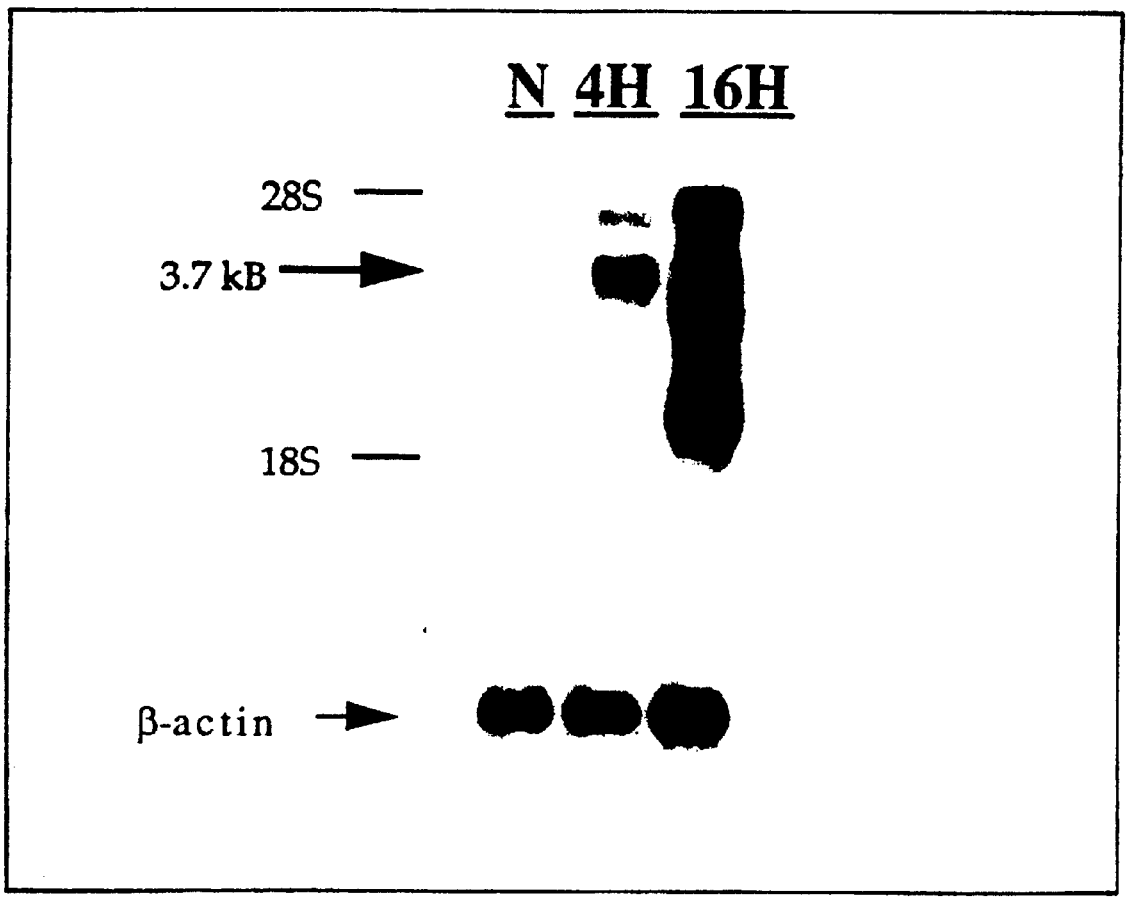
FIG. 4 is a photograph of a Northern blot analysis of VEGF mRNA species expressed under conditions of severe hypoxia. C6 cells were grown under normoxia (N) or were exposed to 1% oxygen for 4 hours (4 H) or 16 hours (16 H). 5 µg of poly (A)$^+$ RNA from each culture was subjected to a Northern blot analysis using a VEGF-specific probe. The bold arrow points at the most frequently encountered 3.7 kB VEGF mRNA.

Alternative splicing of VEGF RNA results in formation of four mRNA species encoding different isoforms of the protein [Ferrara et al., 1991]. These mRNAs differ with respect to the presence or absence of coding exons 6 and 7 and are coordinately regulated by hypoxia (i.e. production of all isoforms is equally increased by hypoxia) [Banai et al., 1994; Minchenko et al., 1994]. There is no evidence, however, for the existence of variant forms of VEGF mRNA which differ with respect to the 5'-3'-untranslated regions. Yet, when cells are grown under conditions of severe ischemia, additional new forms of VEGF mRNA accumulate, the size of which can not be accounted for by changes in the coding region alone (FIG. 4). Interestingly, smaller VEGF mRNAs have been encountered before but have generally been ignored [e.g. Mazure, 1996; Finkenzeller, 1995]. The appearance of these smaller mRNAs suggested that they might represent transcripts with a truncated 5'UTR, or a truncated 3'UTR, or both.

To examine the possibility that splice variants of the 5'UTR exist, mRNA from hypoxic NIH 3T3 cells was amplified by RT-PCR using oligonucleotide primers derived from the most distal and most proximal segments of the full length 5'UTR. The use of this primer combination assured that only 5'UTR sequences are amplified and only of transcripts sharing the same 5' terminus. Several fragments were amplified and verified by blot-hybridization as containing VEGF 5'UTR sequences. However, only one amplified fragment was cloned and further analyzed. The 163 nucleotides long sequence of this modified 5'UTR, designated SP163 (SEQ ID No:7), is shown in Table 1. Alignment of this sequence with that of the full length 5'UTR suggested that it was generated by a splicing event that juxtaposed the 5' cap-containing segment of 31/32 nucleotide next to the 132/131 nucleotides preceding the initiator AUG codon. The experiments described below demonstrate the performance of the SP163 element as a mediator of cap-independent translation and its activity as a translation enhancer.

Example 3

SP163 Function as IRES

As described in Examples 1 and 2, SP163 was identified during the search for possible IRES sequences in the 5'UTR of VEGF. A series of further experiments were designed to characterize its activity as an IRES. The ability of SP163 to promote expression that is derived from the ribosomal entry site was tested in the bi-cistronic vector pBIC-LS. pBIC-LS contains luciferase gene as the first cistron and SeAP as the second cistron, in between is a multiple cloning site that allows the introduction of potential IRES sequences. The IRES activity of SP163 was compared to the parental vector pBIC/LS and to the entire 5'UTR of VEGF from which it was derived. It has stronger activity than the entire 5'UTR. The three plasmid pBIC/LS, pBIC/L5'UTRS and pBIC/L163S were introduced transiently into C6 glioma cells. SeAP activity reflects the IRES effectiveness, and luciferase activity is used to normalize in the overall changes in transcription. SP163 was generally over 5–8 fold more active as an IRES than the entire 5'UTR.

Figure 5:
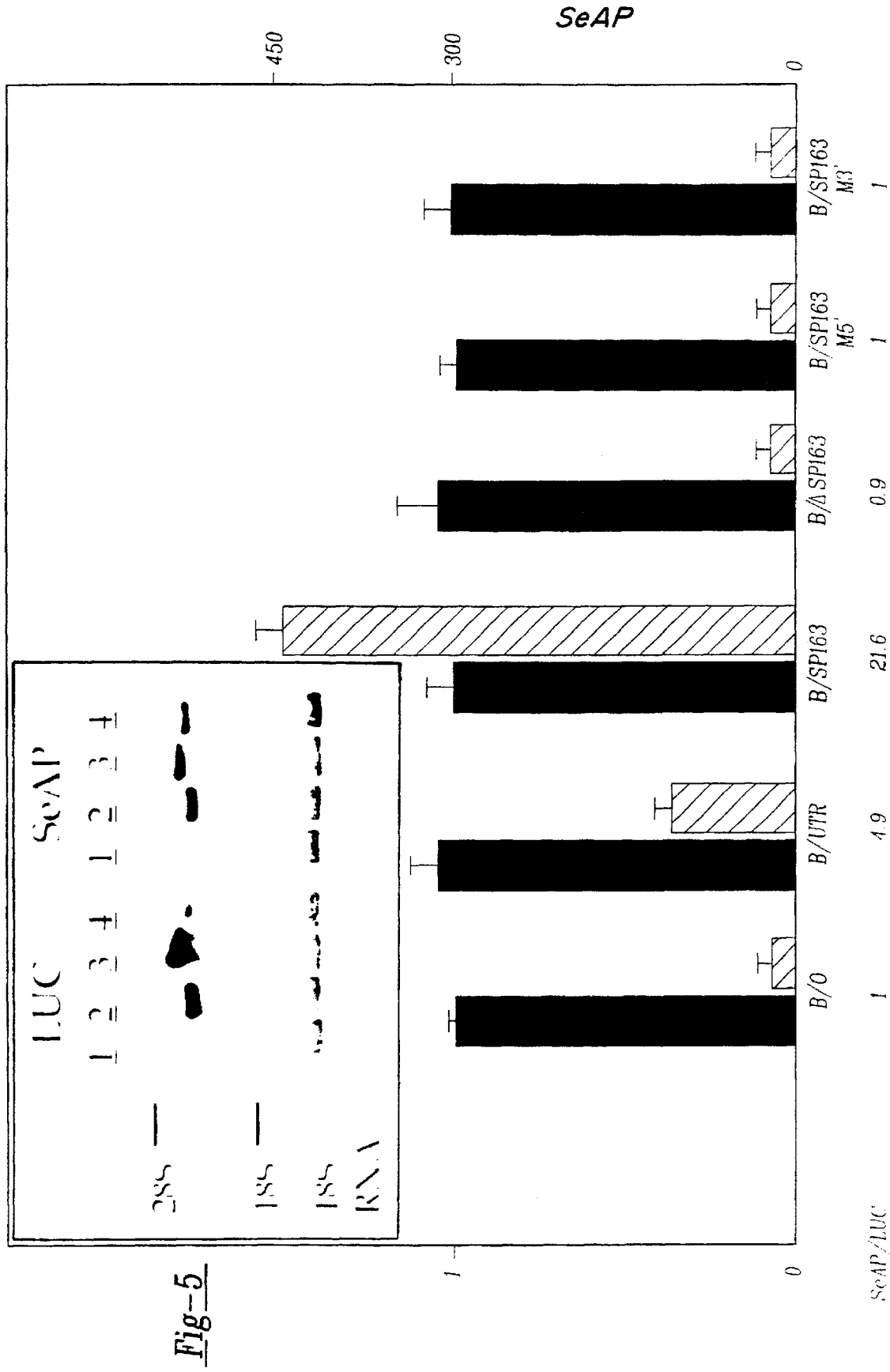
FIG. 5 is a graph of IRES activity of SP163. 293 cells were transiently transfected with each of the indicated bicistronic plasmids and SeAP and LUC activities were determined 36 h post-transfection as described under 'Methods'. Results are expressed as a SeAP/LUC ratio and represent the average of 4 independent transfections for each plasmid. Plasmid designations are as shown in FIG. 1. B/ΔSP163 is a deletion mutant of SP163 missing the first 31 nucleotides. B/SP163/M5' is a substitution mutation wherein the 9 nucleotides from the 5' teminus of SP163 are substituted. B/SP163/M3' is a substitution mutation of the 5 nucleotides from the 3' terminus. Inset is a photograph of a Northern blot analysis with a SeAP-specific probe and a LUC-specific probe performed on 20 µg of the total RNA extracted from transfected 293 cells 36 h post-transfection. Lane 1—mock-transfected cells; lane 2—B/0-transfected cells; lane 3—B/UTR-transfected cells; lane 4—B/SP163-transfected cells.

The SP163 element was inserted into the ICS region of the same bicistronic vector used to analyze the 'conventional' 5'UTR (Example 1). This plasmid, designated B/SP163 was transfected into the human 293 cell line alongside with plasmid B/0 (serving as a negative control) and plasmid B/UTR (for comparison of relative IRES strength). Proteins encoded by the first and second cistrons were quantified following a transient transfection (FIG. 5). Again, only negligible SeAP activity could be detected in cells transfected with B/0, confirming a non-leaky ribosome scanning through the first cistron. Consistent with the results of the stable transfections shown in FIGS. 2A–B, the full-length 5'UTR directed a considerable level of SeAP production also in cells of human origin. Remarkably and unexpectedly, SP163 was 5-fold more efficient than the full-length 5'UTR as IRES element.

Figure 6:
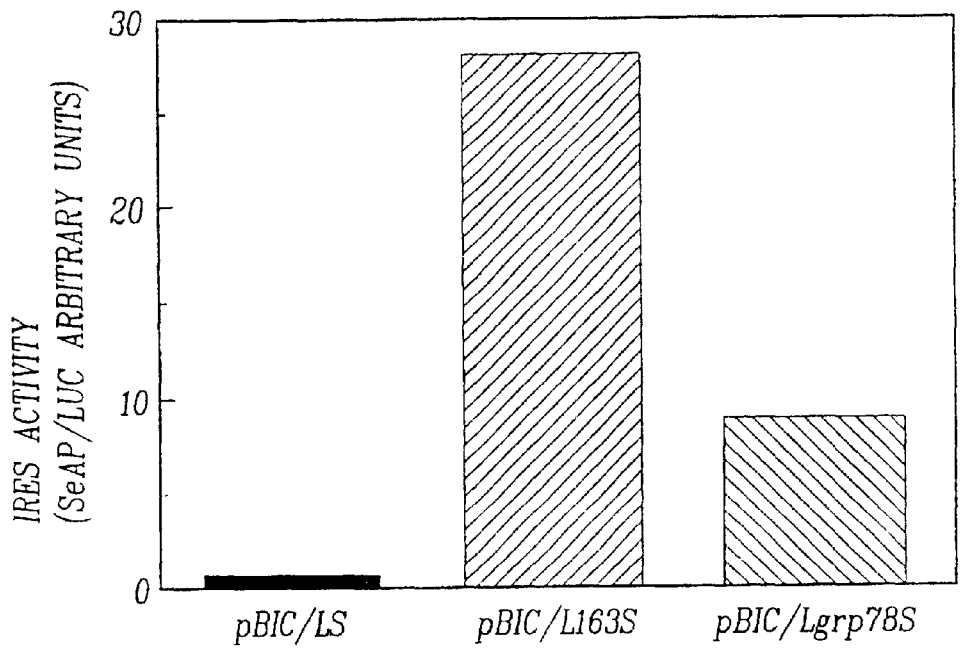
FIG. 6 is a graph showing the effectiveness of SP163 when compared to another cellular IRES, that of the grp78 gene.

SP163 also functions as an IRES in the CHO cell. pBIC-LS contains neomycin genes that allow selection following introduction and establishment of the vector into cells. Plasmid pBIC/LS (parental) and pBIC/L163S were transfected into the CHO cell. In this experiment, the effectiveness of SP163 was compared to another cellular IRES, that of the grp78 gene. The result of this experiment, presented in FIG. 6, shows that SP163 function as an IRES after its establishment in the host genome. Its activity is over 25-fold over the background (pBIC/LS). Moreover, it is three-fold more effective as an IRES than the IRES of grp78, the best characterized cellular IRES known to date.

RNA blot-hybridization analysis was performed to assure that SP163-directed translation of SeAP was by internal ribosome entry. As shown in FIG. 5 (inset), a single mRNA species, corresponding in size to the expected size of a bicistronic B/SP163 mRNA co-hybridized with the LUC-specific probe and the SeAP-specific probe and no mono-cistronic SeAP mRNA could be detected. This result indicated that SeAP was translated from a bicistronic RNA using a SP163-directed internal ribosome entry.

Example 4

Activity of SP163

Activity in transient expression in cell lines of different species. Transient transfection is commonly used for characterization of the function of a cloned gene. In order to analyze the ability of SP163 to stimulate expression in transient transfection, 5 µg of plasmid DNA of the vectors pBKCS and pBKC163S was introduced into different cell lines by liposomes mediated transfection. Twenty four hours after the transfection, the growth media was changed and SeAP activity was measured. Expression was tested in the following cell lines: Rodents—CHO (hamster) and C6 glioma, Primates-Vero, Human Hek 293 and Hela.

Figure 7:
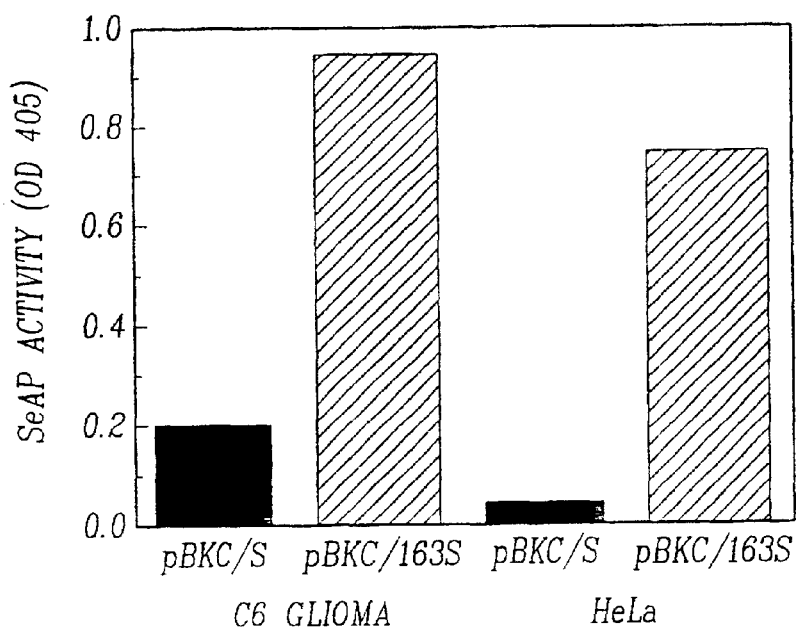
FIG. 7 is a graph showing results obtained for two representative species, rat C6 cells and human Hela cells.

The results obtained indicate that in all the species tested, the addition of SP163 to the pBKC/S vector leads to a significant stimulation of expression of 5–10 fold as measured by the reporter SeAP. In the rat C6 glioma line SP163 addition leads to a 5-fold increase in SeAP activity (FIG. 7), whereas in the Hela Cell line more than 10-fold stimulation was observed (FIG. 7). The conclusion is that SP163 can be a useful addition to any vectors that are used to analyze expression of a target gene in transient transfection.

Effect of SP163 in stable expression in mono-cistronic vectors. Production of recombinant proteins for commercial purposes is done in systems where expression of the target gene is stable. The parental expression vector pBKC/S includes the neomycin gene that confers resistance to G418 (FIG. 1). This feature was used to introduce the pBKC/S and pBKC/163S plasmids into CHO and C6 glioma cell lines. CHO is the preferred mammalian cell line for the production of biopharmaceuticals. Plasmid DNA of the vectors pBKC/S and pBKC163S was introduced by the liposome method and colonies resistant to G418 were selected and analyzed. SeAP expression levels were tested in pools of the G418 resistant colonies. The results shown in FIGS. 8A–B and FIG. 11 demonstrate that the enhancing performance of SP163 is retained when the expression vector is integrated into the host cell genome. SP163 insertion in the 5' of the SeAP reporter gene led to a 5–20 fold stimulation of expression in CHO and C6 glioma cells.

Figure 9:
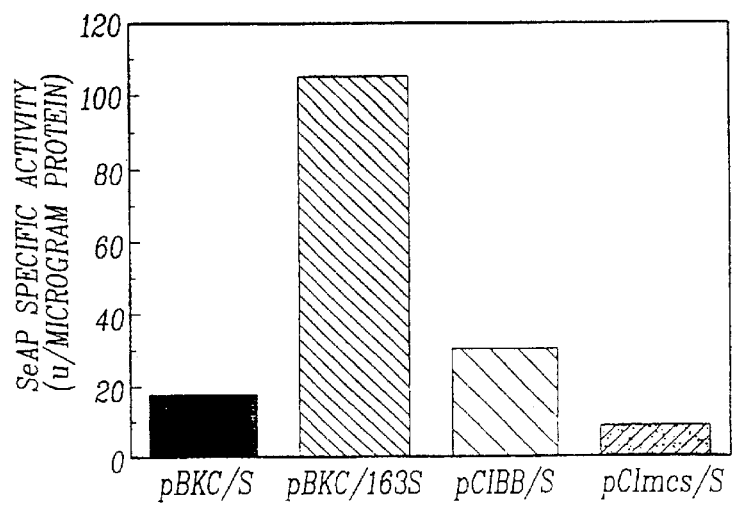
FIG. 9 is a graph showing the relative stimulation of SeAP activity and SeAP activity in pBKC/163S was 4 fold higher than pCIBB/S and over 6-fold higher than pCImc/S.

The relative stimulation of SeAP activity (FIG. 9), observed in plasmid pBKC/163S is not restricted to the comparison with plasmid pBKC/S. SeAP activity of pBKC/163S was compared in stable transfection in CHO cells with an additional two plasmids pCIBB/S to the basic expression vector and pCImc/S (pCIBB with the multiple cloning site that was engineered into pBKC to exclude the possibility that this segment is responsible for the enhancing effect). As shown in FIG. 9, SeAP activity in pBKC/163S was four fold higher than pCIBB/S and over six-fold higher than pCImc/S.

Example 5

SP163 Acts at the Level of Translation in Mono-Cistronic and Bi-Cistronic Vectors SP163 enhances expression by increasing translation efficiency and not by influencing the abundance of mRNA due to increased stability or increased transcription. This was shown by Northern blot analysis of the amounts of mRNA of the reporter genes (SeAP and Luc) that are transcribed from the different vectors. The results are shown in FIGS. 10A–C.

Figure 10A:
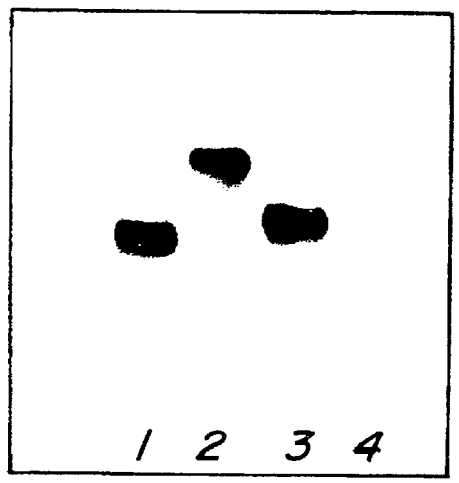
FIGS. 10A–10C are photographs of gel electrophoresis showing Northern blot analysis of the amounts of mRNA of the reporter genes (SeAP and Luc) that are transcribed from the different vectors.

The results for the mono-cistronic context are presented in FIG. 10A. The amounts of mRNA expressed by plasmids pBKC/S (control) [lane 1[,pBKC/5'UTR/S [lane 2], pBKC/

163/S [lane 3] and mock transfected cells [lane 4] were the same. The differences in the length of mRNA generated by the different vectors reflect the addition in length due to the insert sizes (1 Kb in pBKC/5'UTR/S and 163 bp in pBKC/163/S).

Figure 10B:
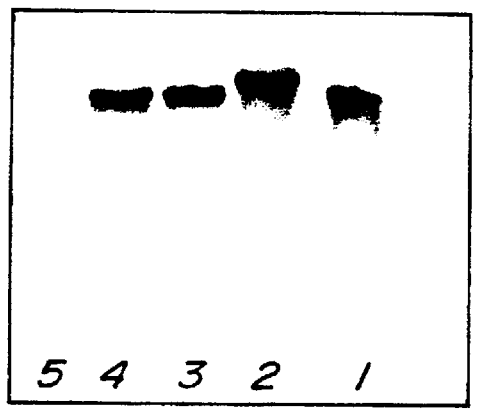
Figure 10C:
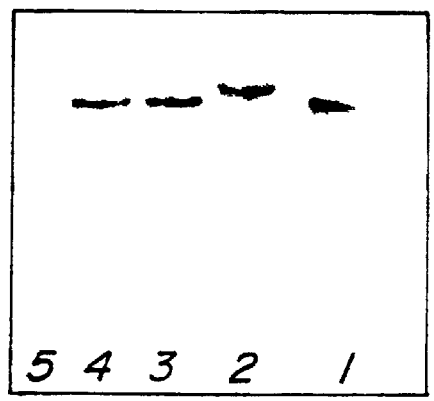

The results for the bi-cistronic vector that are shown in FIGS. 10B and 10C indicate that the amounts of mRNA transcribed by the different cistrons are at the same level. FIG. 10B shows results for the luciferase gene representing the first cistron and panel c for the second cistron SeAP (see FIG. 1 for details). Each cistron was analyzed with the corresponding probe by Northern blot analysis. The amounts of mRNA were the same for all plasmids: pBIC/LS (control) lane 1, pBIC/LUTRS lane 2, pBIC/L163S lane 3, pBIC/Lgrp78S (lane 5 is mock transfected cells).

As can be seen from the results in FIGS. 10B and C, only one mRNA is encoded by the bi-cistronic vectors without the IRES DNA (lane 1) or with the different DNA fragments tested (lane 2, 5'UTR, lane 3 SP163 and lane 4 grp78), clearly indicating that SP163 functions as an IRES and that the stimulation of expression results from increased translation efficiency of the transcript and not from increase in the amount of the bi-cistronic mRNA or from the generation of a new SeAP mRNA that can be theoretically derived if SP163 has promoter activity.

Example 6

Translational Enhancement by SP163

Figure 11:
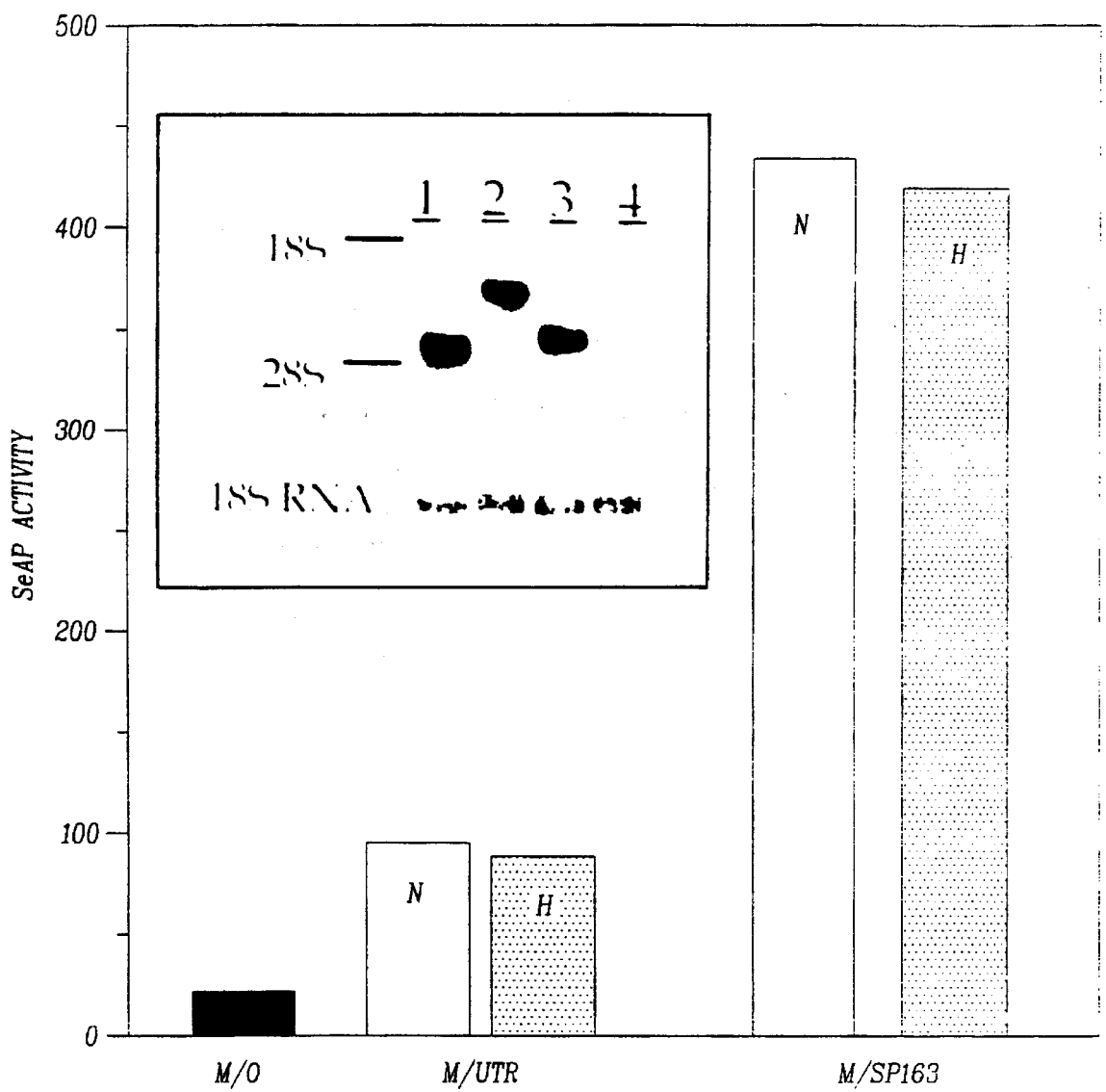
FIG. 11 is a graph showing translation enhancing activity of VEGF 5'UTR sequences under normal (N) and hypoxia (H) conditions. C6 cells were stably transfected with the monocistronic constructs indicated. SeAP activity was analyzed in pools of transfected clones as described under 'Methods' and values were standardized to total protein. For analysis of SeAP activity under hypoxia, cells were shifted to 1% oxygen 24 hours before sampling. Inset is a photograph of Northern blot analysis of SeAP-containing mRNAs in stably-transfected pools. Lane 1—M/0-transfected cells; lane 2—M/UTR-transfected cells; lane 3—M/SP163-transfected cells; lane 4—non-transfected cells.

The possibility that the 5'UTR of VEGF (both the full length form and SP163) act as a translational enhancer was examined by testing its ability to augment translation of a monocistronic mRNA. To this end, the full-size 5'UTR or SP163 was inserted between a CMV promoter and the coding region of SeAP in the context of a monocistronic vector (see FIG. 1). These constructs, designated M/5'UTR and M/SP163 respectively, were transfected into C6 cells and analyzed for SeAP production in pools of stably-transfected clones. Analysis of RNA extracted from transfected cells detected similar levels of SeAP-containing mRNA which was represented in each case by a single band of the expected size (FIG. 11, inset). In contrast, the amount of SeAP activity released to the culture medium varied greatly according to the nature of the insert. Thus, the full-length 5'UTR augmented translation of SeAP by 5-fold and SP163 enhanced SeAP translation much greater. In the experimental results shown in FIG. 11 enhancement by SP163 was 25-fold and in other experiments (not shown) enhancement was up to 40-fold.

Considerations discussed above led to the examination of whether these elements also function as translational enhancers under conditions of hypoxic stress. As shown in FIG. 11, enhancement of SeAP translation was unaffected by growth under conditions of severe hypoxia.

Figure 8A:
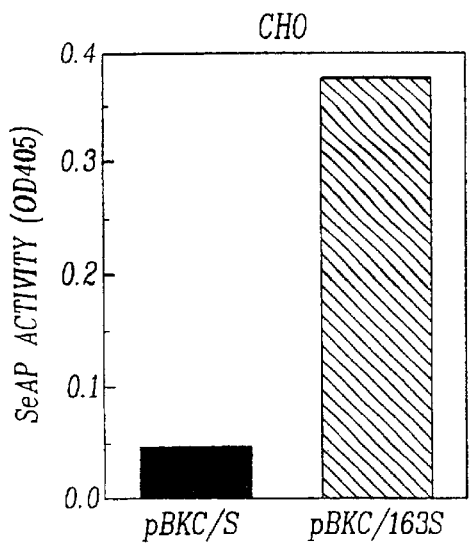
FIGS. 8A–8B are graphs showing that the enhancing performance of SP163 is retained when the expression vector is stabely integrated into the host cell genome.
Figure 8B:
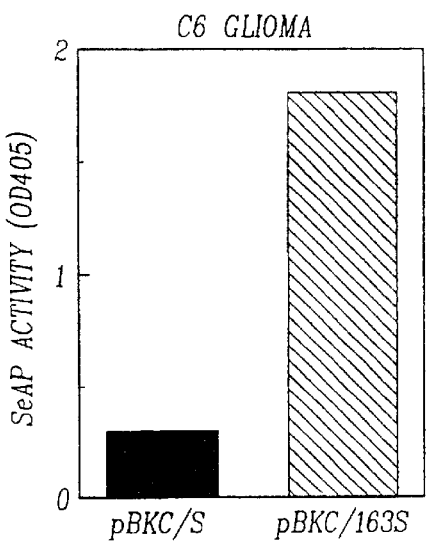

To demonstrate that SP163 is a strong translational enhancer in additional cell types, the same constructs were also transfected into human 293 cells (FIG. 7) and hamster CHO cells (FIG. 8A). SP163 acted as a strong translation enhancer in these cells as well, augmenting SeAP production to a level comparable to that shown for C6 cells (data not shown).

Throughout this application, various publications, are referenced by citation and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

SEQUENCE OF THE SP163 ELEMENT (SEQ ID No:7)

```
          10        20        30 ↓↓
AGCGCAGAGGCTTGGGGCAGCCGAGCGGCAGCCAGGCCC
    40        50        60        70
CGGCCCGGGCCTCGGTTCCAGAAGGGAGAGGAGCCCGCC
    80        90        100       110
AAGGCGCGCAAGAGAGCGGGCTGCCTCGCAGTCCGAGCC
    120       130       140       150
GGAGAGGGAGCGCGAGCCGCGCCGGCCCCGGACGGCCTC
    160
CGAAACC ATG
```

The oligonucleotide primers that were used for amplification of SP163 are underlined. These oligonucleotides correspond to the respective boundaries of the 1014 nucleotide long mouse VEGF 5'UTR. The initiation ATG condon is boxed. Arrows point at two possible locations of a presumptive splice junction. Nucleotide 1 of SP163 corresponds to nucleotides 1218 of the mouse VEGF gene, GeneBank accession U41383, while nucleotide 163 of the SP163 fragment corresponds to nucleotides 2231 of the mouse gene.

TABLE 2

BICISTRONIC AND MONOCISTRONIC CONSTRUCTS

| Bicistronic constructs | Insert | Monocistronic constructs |
|---|---|---|
| B/0 | NONE | M/0 |
| B/UTR | 1 VEGF 5' UTR 1014 | M/UTR |
| B/SP163 | 1 SP163 163 | M/SP163 |
| B/BiP | 1 BiP 5' UTR 221 | (ND) |

Designations of bicistronic and monocistronic constructs used in the Examples. The nucleotide numbers inside the rectangles represent the insert length. ND—not done.

REFERENCES

Aiello, et al. (1994). Vascular endothelial growth factor in ocular fluid of patients with diabetic retinopathy and other disorders [see comments]. N. Engl J Med 331:1480–7.
Alon, et al. (1995). Vascular endothelial growth factor acts as a survival factor for newly formed retinal vessels and has implications for retinopathy of prematurity. Nat Med 1:1024–8.
Banai, et al. (1994). Upregulation of vascular endothelial growth factor expression induced by myocardial ischemia: implications for coronar angiogenesis. Cardiovasc Res 28:1176–9.

Benda, et al. (1968). Differentiated rat glial cell strain in tissue culture. Science 161:370–74.

Bernstein, et al. (1997). PDGF2/c-sis mRNA Leader Contains a Differentiation-linked Internal -Ribosomal Entry Site (D-IRES). J. Biol. Chem. 272:9356–62.

Carmeliet, et al. (1996). Abnormal blood vessel development and lethality in embryos lacking a single VEGF allele. Nature 380:435–9.

Chirgwin, et al. (1979). Isolation of biologically active ribonucleic acid from sources enriched in ribonuclease. Biochemistry 18:5294–99.

Ehrenfeld, (1996). Initiation of Translation by Picornavirus RNAs. In Translational Control, J. W. B. Hershey, M. B. Mathews and N. Sonenberg, eds. (NY: Cold Spring Harbor Laboratory Press), pp. 549–73.

Ferrara, et al. (1991). The vascular endothelial growth factor family of polypeptides. J. Cell Biochem 47:211–8.

Ferrara, et al. (1996). Heterozygous embryonic lethality induced by targeted inactivation of the VEGF gene. Nature 380:439–42.

Finkenzellen, et al. (1995). Hypoxia-induced transcription of the vascular endothelial growth factor gene is independent of functional AP-1 transcription factor. Biochem. Biophys. Res. Comm. 208:432–439.

Forsythe, et al. (1996). Activation of vascular endothelial growth factor gene transcription by hypoxia-inducible factor 1. Mol Cell Biol 16:4604–13.

Frangakis and Kimelberg (1984). Dissociation of neonatal rat brain by dispase for the preparation of primary astrocyte culture. Neurochem. Res. 9:1689–98.

Gan and Rhoads (1996). Internal Initiation of Translation Directed by the 5'-Untranslated Region of the mRNA for eIF4G, a factor Involved in the Picornavirus-induced Switch from Cap-dependent to Internal Initiation. J. Biol. Chem. 271:623–6.

Heacock and Sutherland (1988). Induction and modulation of oxygen regulated protein synthesis. In International Radiation Research Society Meeting (Edinburgh, Scotland).

Ikeda, et al (1995). Hypoxia-induced transcriptional activation and increased mRNA stability of vascular endothelial growth factor in C6 glioma cells. J. Biol Chem 270:19761–6.

Jackson, (1996). A Comparative View of Initiation Site Selection mechanisms. In Translational Control, J. W. B. Hershey, M. B. Mathews and N. Sonenberg, eds. (NY: Cold Spring Harbor Laboratory Press), pp. 71–112.

Jang, et al (1988). A segment of the 5' nontranslated region of encephalomyocarditisvirus RNA directs internal entry of ribosomes during in vitro translation. J. Virol. 62:2636–43.

Jang, et al (1989). Initiation of Protein Synthesis by Internal Entry of Ribosomes into the 5' nontranslated Region of Encephalomyocarditis Virus RNA In Vivo. J. Virol. 63:1651–60.

Jordan, et al. (1996). Transfecting mammalian cells: optimization of critical parameters affecting calcium-phosphate precipitate formation. Nuc. Acid. Res. 24:596–601.

Kozak, (1991). An Analysis of Vertebrate mRNA Sequences: Intimations of Translational Control. J. Cell. Bio. 115:887–903.

Kraggerud, et al. (1995). Regulation of protein synthesis in human cells exposed to extreme hypoxia. Anticancer Res. 15:683–6.

Le and Maizel (1997). A common RNA structural motif involved in the internal initiation of translation of cellular mRNAs. Nuc. Acid. Res. 25:362–69.

Levy et al, 1995. Transcriptional regulation of the rat vascular endothelial growth factor gene by hypoxia. J. Bio. Chem. 270:13333–13340.

Lindquist (1986). The heat-shock response. Ann. Rev. Biochem. 55:1151–91.

Macejak and Sarnow (1991). Internal initiation of translation mediated by the 5' leader of a cellular mRNA. Nature 353:90–94.

Mathews et al (1996). Origins and targets of translational control. In Translational Control, J. W. B. Hershey, M. B. Mathews and N. Sonenberg, eds. (NY: Cold Spring Harbor Laboratory Press), pp. 1–29.

Matzura and Wennborg (1996). RNAdraw: an integrated program for RNA secondary structure calculation and analysis under 32-bit Microsoft Windows. CABIOS 12:247–9.

Mazure, et al. (1996). Oncogenic transformation and hypoxia synergistically act to modulate vascular endothelial growth factor expression. Cancer Res 56:3436–3340.

Meyuhas, et al. (1987). Glucocorticoids selectively inhibit translation of ribosomal protein and mRNAS in p1798 lymphosarcoma+++cells. Mol. Cell. Biol. 7:2691–99.

Meyuhas, et al. (1996). Translational control of ribosomal protein mRNAs in eukaryotes. In Translational Control, J. W. B. Hershey, M. B. Mathews and N. Sonenberg, eds. (NY: Cold Spring Harbor Laboratory Press), pp. 363–388.

Minchenko, et al. (1994). Hypoxic stimulation of vascular endothelial growth factor expression in vitro and in vivo. Lab Invest. 71:374–9.

Minty, et al. (1981). Mouse actin messenger RNAs. Construction and characterization of a recombinant plasmid molecule containing a complementary DNA transcript of mouse alpha-actin mRNA. J. Biol. 256:1008–14.

Mountford and Smith (1995). Internal ribosome entry sites and dicistronic RNAs in mammalian trangenesis. TIG 11(5):179–184.

Oh, et al. (1992). Homeotic gene Anntennapedia mRNA contains 5'-noncoding sequences that confer translational initiation by internal ribosome binding. Genes. Dev. 6:1643–53.

Oh and Sarnow (1993). Gene Regulation: tranlational initiation by internal ribosome binding. Curr Opinion Genetics Devel 3:295–300.

Pain (1996). Initiation of protein synthesis in eukaryotic cells. Eur. J. Biochem. 236:747–71.

Pelletier and Sonenberg (1988). Internal initiation of translation of eukaryotic mRNA directed by a sequence derived from poliovirus RNA. Nature 334:320–325.

Pe'er, et al. (1995). Hypoxia-induced expression of VEGF by retinal cells is a common factor in neovascularizing ocular diseases. Lab. Invest. 72:638–645.

Shima et al., 1995. The mouse gene for vascular endothelial growth factor. J. Biol. Chem. 271:3877–3883.

Shweiki, et al. (1995). Induction of vascular endothelial growth factor expression by hypoxia and by glucose deficiency in multicell spheroids: implications for tumor angiogenesis. Proc. Natl. Acad. Sci. USA 92:768–72.

Sonenberg (1996). mRNA 5' Cap-binding Protein eIF4E and control of Cell Growth. In Translation Control, J. W. B. Hershey, M. B. Mathews and N. Sonenberg, eds. (NY: Cold Spring Harbor Laboratory Press), pp. 245–269.

Stein, et al. (1995). Stabilization of vascular endothelial growth factor mRNA by hypoxia and hypoglycemia and coregulation with other ischemia-induced genes. Mol. Cell. Biol. 15:5363–8.

Stone, et al. (1995). Development of retinal vasculature is mediated by hypoxia-induced vascular endothelial growth factor (VEGF) expression by neuralgia. J Neurosci 15:4738–47.

Teerink, et al. (1995). The human insulin-like growth factor II leader contains an internal ribosomal entry site. Biochim. Biophys. Acta. 1264:403–8.

Tischer, et al., 1991. The human gene for vascular endothelial growth factor. J. Biol. Chem. 266:11947–11954.

Vagner, et al. (1995). Alternative translation of human fibroblast growth factor 2 mRNA occurs by internal entry of ribosomes. Mol. Cell. Biol. 15:35–44.

Ye, et al. (1997). Ultrabithorax and Anntennapedia 5' Untranslated Regions Promote Developmentally Regulated Internal Translation Initiation. Mol. Cell. Biol. 17:1714–21.

What is claimed is:

1. An isolated and cloned translation control element consisting essentially of the nucleotide sequence as set forth in SEQ ID No:7.

2. The translation control element as set forth in claim 1 wherein the sequence controls cap-independent mRNA translation via an internal ribosome entry site (IRES).

3. An expression vector comprising the translation control element as set forth in claim 1 operatively linked to a gene sequence to be expressed.

4. An expression vector comprising at least two nucleic acid sequences to be translated and said translation control element as set forth in claim 1 and wherein said translation control element is operatively linked to at least one of the sequences to be translated.

5. The expression vector as set forth in claim 4 wherein a single promoter is included.

6. A method for facilitating cap-independent translation of mRNA comprising including in an expression cassette a translation control element consisting essentially of the nucleotide sequence as set forth in SEQ ID No:7.

7. An isolated internal ribosome entry site (IRES) consisting essentially of the nucleotide sequence as set forth in SEQ ID No:7.

8. A method for facilitating preferential translation of a gene of interest over the bulk of cellular mRNAs by including in an expression vector a translation control element consisting essentially of the nucleotide sequence as set forth in SEQ ID No:7 operatively linked to the gene of interest and expressing the vector in host cells with reagents that inhibit cap-dependent translation.

9. A method for facilitating preferential translation of a gene of interest over the bulk of cellular mRNAs by including in an expression vector a translation control element consisting essentially of the nucleotide sequence as set forth in SEQ ID No:7 operatively linked to the gene of interest and expressing the vector in host cells under conditions of cellular stress.

10. An isolated and cloned translation control element consisting essentially of a nucleotide sequence at least 80% homologous to SEQ ID No:7.

11. The translation control element as set forth in claim 10 wherein the sequence controls cap-independent mRNA translation via an internal ribosome entry site (IRES).

12. An expression vector comprising a translation control element as set forth in claim 10 operatively linked to a gene sequence to be expressed.

13. An expression vector comprising at least two nucleic acid sequences to be translated and a translation control element as set forth in claim 10 and wherein said translation control element is operatively linked to at least one of the sequences to be translated.

14. The expression vector as set forth in claim 13 wherein a single promoter is included.

15. A method for facilitating cap-independent translation of mRNA comprising including in an expression cassette a translation control element consisting essentially of a nucleotide sequence at least 80% homologous to SEQ ID No:7.

16. An isolated internal ribosome entry site (IRES) consisting essentially of a nucleotide sequence at least 80% homologous to SEQ ID No:7.

17. A method for facilitating preferential translation of a gene of interest over the bulk of cellular mRNAs by including in an expression vector a translation control element consisting essentially of a nucleotide sequence at least 80% homologous to SEQ ID No:7 operatively linked to the gene of interest and expressing the vector in host cells with reagents that inhibit cap-dependent translation.

18. A method for facilitating preferential translation of a gene of interest over the bulk of cellular mRNAs by including in an expression vector a translation control element consisting essentially of a nucleotide sequence at least 80% homologous to SEQ ID No:7 operatively linked to the gene of interest and expressing the vector in host cells under conditions of cellular stress.

* * * * *

UNITED STATES PATENT AND TRADEMARK OFFICE
CERTIFICATE OF CORRECTION

PATENT NO. : 6,653,132 B1
DATED : November 25, 2003
INVENTOR(S) : Eli Keshet, Ilan Stein and Ahuva Itin It is certified that error appears in the above-identified patent and that said Letters Patent is hereby corrected as shown below:

Title page,
Item [73], Assignee, "QBI Enterprises, Ltd." should read -- Yissum Research Development Company of the Hebrew University of Jerusalem and QBI Enterprises, Ltd. --.

Signed and Sealed this

Twenty-second Day of February, 2005

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial sequence
<220> FEATURE:
<221> NAME/KEY: Artificial sequence
<222> LOCATION: (1)..(22)
<223> OTHER INFORMATION: primer

<400> SEQUENCE: 1
ctcgagcgca gaggcttggg gc                                               22

<210> SEQ ID NO 2
<211> LENGTH: 22
<212> TYPE: DNA
<213> ORGANISM: Artificial sequence
<220> FEATURE:
<221> NAME/KEY: Artificial sequence
<222> LOCATION: (1)..(22)
<223> OTHER INFORMATION: primer

<400> SEQUENCE: 2
ccatggtttc ggaggccgtc cg                                               22

<210> SEQ ID NO 3
<211> LENGTH: 27
<212> TYPE: DNA
<213> ORGANISM: Artificial sequence
<220> FEATURE:
<221> NAME/KEY: Artificial sequence
<222> LOCATION: (1)..(27)
<223> OTHER INFORMATION: primer

<400> SEQUENCE: 3
ctcgagaggt cgacgccggc caagaca                                          27

<210> SEQ ID NO 4
<211> LENGTH: 27
<212> TYPE: DNA
<213> ORGANISM: Artificial sequence
<220> FEATURE:
<221> NAME/KEY: Artificial sequence
<222> LOCATION: (1)..(27)
<223> OTHER INFORMATION: primer

<400> SEQUENCE: 4
ccatggcttg ccagccagtt gggcagc                                          27

<210> SEQ ID NO 5
<211> LENGTH: 21
<212> TYPE: DNA
```

```
<213> ORGANISM: Artificial sequence
<220> FEATURE:
<221> NAME/KEY: Artificial sequence
<222> LOCATION: (1)..(21)
<223> OTHER INFORMATION: primer

<400> SEQUENCE: 5
gagagaatga gcttcctaca g                                              21

<210> SEQ ID NO 6
<211> LENGTH: 21
<212> TYPE: DNA
<213> ORGANISM: Artificial sequence
<220> FEATURE:
<221> NAME/KEY: Artificial sequence
<222> LOCATION: (1)..(21)
<223> OTHER INFORMATION: primer

<400> SEQUENCE: 6
tcaccgcctt ggcttgtcac a                                              21

<210> SEQ ID NO 7
<211> LENGTH: 166
<212> TYPE: DNA
<213> ORGANISM: Artificial sequence
<220> FEATURE:
<221> NAME/KEY: Artificial sequence
<222> LOCATION: (1)..(166)
<223> OTHER INFORMATION: SP163

<400> SEQUENCE: 7
agcgcagagg cttggggcag ccgagcggca gccaggcccc ggcccgggcc tcggttccag     60
aagggagagg agcccgccaa ggcgcgcaag agagcgggct gcctcgcagt ccgagccgga   120
gagggagcgc gagccgcgcc ggccccggac ggcctccgaa accatg                  166
```